United States Patent
To et al.

(10) Patent No.: US 11,457,846 B2
(45) Date of Patent: Oct. 4, 2022

(54) TESTER FOR AN OPTICAL MEASURING DEVICE

(71) Applicant: Belun Technology (IP) Company Limited, Hong Kong (HK)

(72) Inventors: Kwan Wai To, Hong Kong (HK); Ka Cheung Kwok, Hong Kong (HK)

(73) Assignee: Belun Technology (IP) Company Limited, Hong Kong (HK)

( * ) Notice: Subject to any disclaimer, the term of this patent is extended or adjusted under 35 U.S.C. 154(b) by 207 days.

(21) Appl. No.: 17/084,649

(22) Filed: Oct. 30, 2020

(65) Prior Publication Data

US 2021/0128028 A1     May 6, 2021

Related U.S. Application Data

(60) Provisional application No. 62/928,470, filed on Oct. 31, 2019.

(51) Int. Cl.
*A61B 5/1495*     (2006.01)
*A61B 5/1455*     (2006.01)

(52) U.S. Cl.
CPC ........ *A61B 5/1495* (2013.01); *A61B 5/14552* (2013.01); *A61B 2562/0238* (2013.01)

(58) Field of Classification Search
CPC . A61B 5/1495; A61B 5/1455; A61B 5/14552; A61B 2562/0238
See application file for complete search history.

(56) References Cited

U.S. PATENT DOCUMENTS

| | | | |
|---|---|---|---|
| 4,968,137 A | 11/1990 | Yount | |
| 5,166,517 A | 11/1992 | Volgyesi | |
| 5,278,627 A | 1/1994 | Aoyagi et al. | |
| 5,305,744 A | 4/1994 | Pfeiffer et al. | |
| 5,348,005 A | 9/1994 | Merrick et al. | |
| 5,783,821 A | 7/1998 | Costello, Jr. | |
| 5,784,151 A | 7/1998 | Miller et al. | |
| 6,133,994 A | 10/2000 | Mathews et al. | |
| 6,400,973 B1 | 6/2002 | Winter | |
| 6,839,580 B2 | 1/2005 | Zonios et al. | |
| 6,954,664 B2 | 10/2005 | Sweitzer et al. | |

(Continued)

FOREIGN PATENT DOCUMENTS

| | | |
|---|---|---|
| CN | 1542521 A | 11/2004 |
| CN | 1836632 A | 9/2006 |

(Continued)

OTHER PUBLICATIONS

Shuba Dugani et al., "Evaluation of a Pulse Oximeter Sensor Tester", Journal of Clinical Monitoring and Computing, May 18, 2011, p. 1-9.

(Continued)

*Primary Examiner* — Eric F Winakur
(74) *Attorney, Agent, or Firm* — Idea Intellectual Limited; Margaret A. Burke; Sam T. Yip

(57) ABSTRACT

The present document relates to a tester for testing pulse oximeters, wherein the tester is configured for use with a plurality of measuring devices. The tester device may comprise a plurality of light detector sets and a light emitter set, wherein each of the plurality of light detector sets may be used to trigger the light emitter set. Such an arrangement may allow the tester to be used with a transmissive type pulse oximeter as well as with a reflective type pulse oximeter.

18 Claims, 14 Drawing Sheets

(56) References Cited

U.S. PATENT DOCUMENTS

| | | |
|---|---|---|
| 7,346,378 B2 | 3/2008 | Ruiter |
| 7,748,252 B2 | 7/2010 | Wieringa et al. |
| 8,311,601 B2 | 11/2012 | Besko |
| 8,418,524 B2 | 4/2013 | Al-Ali |
| 8,779,349 B2 | 7/2014 | West |
| 9,468,403 B2 | 10/2016 | Ho et al. |
| 2006/0247507 A1 | 11/2006 | Ruiter |
| 2012/0229800 A1 | 9/2012 | West |
| 2014/0288400 A1 | 9/2014 | Diab et al. |
| 2016/0025685 A1 | 1/2016 | Suita et al. |
| 2016/0125766 A1 | 5/2016 | Ogawa et al. |

FOREIGN PATENT DOCUMENTS

| | | |
|---|---|---|
| CN | 1864629 A | 11/2006 |
| CN | 100386054 C | 5/2008 |
| CN | 102389314 A | 3/2012 |
| CN | 203388866 U | 1/2014 |
| CN | 103815917 A | 5/2014 |
| CN | 103271745 B | 5/2015 |
| CN | 204394524 U | 6/2015 |
| CN | 103876748 B | 12/2015 |
| CN | 108095733 A | 6/2018 |
| JP | H067827 B2 | 2/1994 |
| WO | 2019057204 A1 | 3/2019 |

OTHER PUBLICATIONS

"Medical electrical equipment—Part 2-61: Particular requirements for basic safety and essential performance of pulse oximeter equipment", International Standard ISO 80601-2-61, Apr. 1, 2011, p. 61-69.

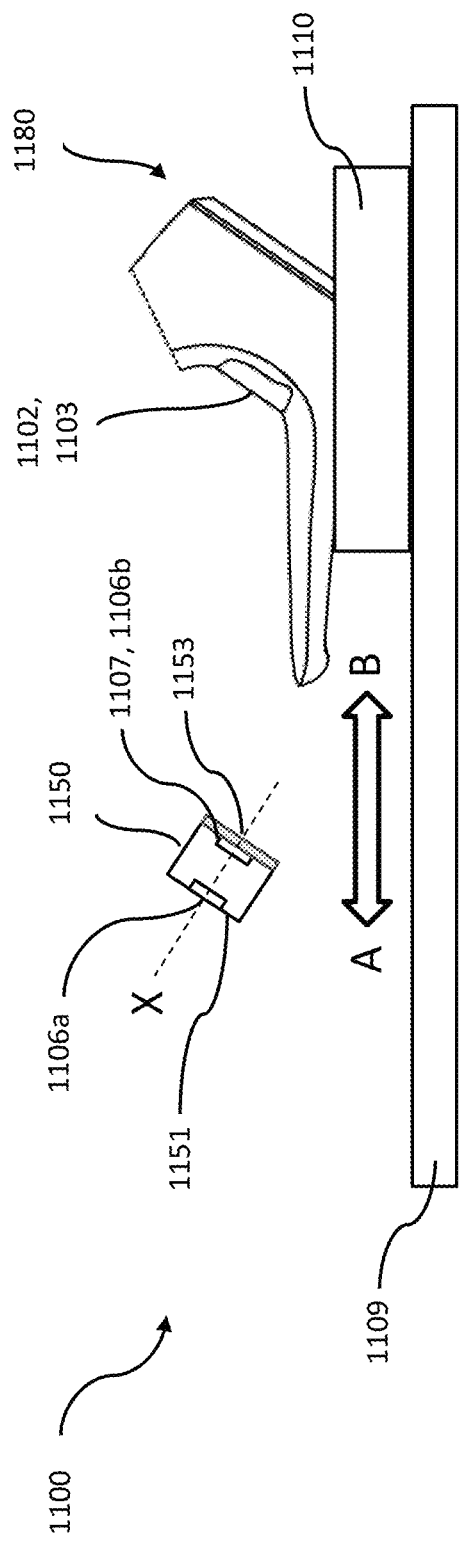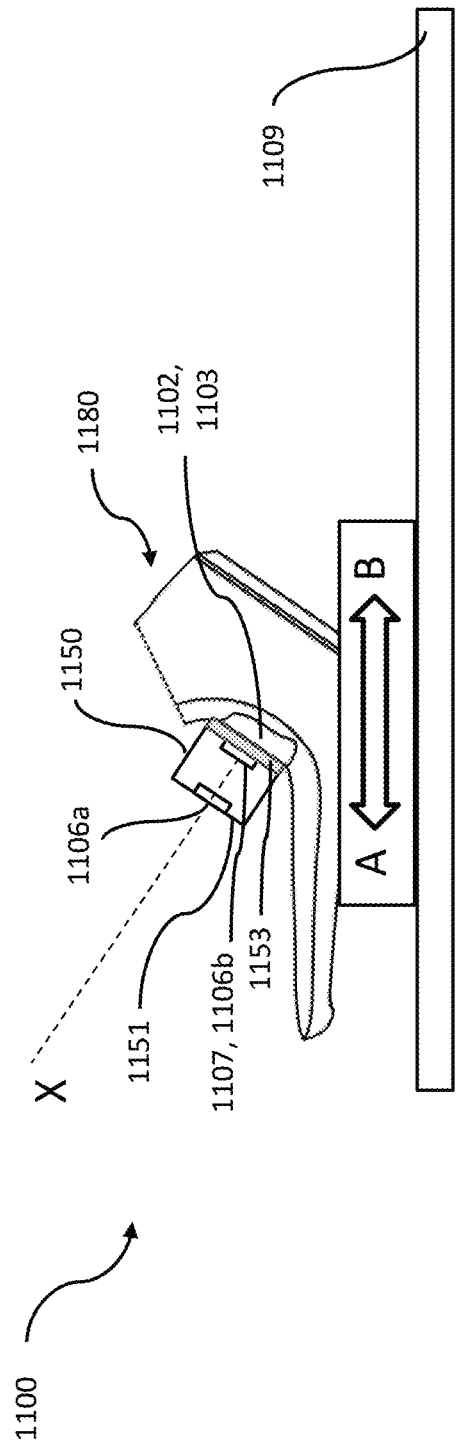

TESTER FOR AN OPTICAL MEASURING DEVICE

CROSS-REFERENCE TO RELATED APPLICATIONS

The present application claims benefit of priority from U.S. Provisional Application No. 62/928,470, filed Oct. 31, 2019, entitled "ADAPTIVE TESTER FOR MEASURING DEVICE" which is incorporated by reference herein in its entirety.

FIELD OF INVENTION

The present technology generally relates to a device for testing an optical measuring apparatus and methods related thereto, such as a tester device for a pulse oximeter or an optical heart rate monitor.

BACKGROUND

Myriad techniques exist for measuring one or more of a user's physiological parameters, as do devices that perform these techniques. Some of these techniques are optical, relying on characteristics of lights and their interaction with human physiology such as light absorbance by blood to infer characteristics of the user's physiological parameters. One example of measurement techniques is pulse oximetry for measuring the blood oxygen saturation (SpO2) and/or other health data. Another is heart rate measurements. These techniques (and corresponding measuring devices) are widely used in a variety of settings including in hospital/clinical settings and/or at home.

A heart rate sensor may include a set of light emitters, such as a light source, e.g., an infra-red light, and a set of light detectors, such as a light detector for detecting a heart rate of a user.

In pulse oximetry, a set of lights, such as a visible light (e.g. 600 nm-750 nm) and an infra-red light (e.g. 850 nm-1000 nm) is emitted at a body part of the user, and a ratio of unabsorbed to absorbed light is used to infer physiological parameters such as the blood oxygen saturation. Thus, a pulse oximeter typically comprises a set of light sources for emitting a set of emitted lights and a set of light detectors for measuring a set of received lights.

It is desirable that any measured health parameters be highly accurate as they may form inputs for the important task of evaluating the user's health. Consequently, a measuring device may be tested for performance by a tester device (or a "tester") to evaluate whether their performance is within predetermined specifications (i.e. "tested" or "verified"). Such testing may occur after production at the factory, and also after deployment, such as in the hospital or clinical settings, or even at home by a visiting technician. Thus, the tester device should ideally be versatile and easy to use.

Some tester devices operate in reverse to in-vivo measuring devices, by emitting a set of predetermined lights, comprising a visible light and an infra-red light, at predetermined parameters (e.g. ratio of intensities) corresponding to a known SpO2 value. A performance of a measuring device may thus be tested by comparing a measured SpO2 value to the predetermined, corresponding SpO2 value from the tester device.

As each tester device will typically be used to test many measuring devices, it is very important that each tester device's performance is accurately validated and calibrated.

Accordingly, there exists a need to develop a tester device that is not only able to be used to accurately, reliably, and repeatably test the measuring device, but also be able to be accurately, reliably, and repeatably have its own performance validated (i.e. "calibrated" and/or "validated").

SUMMARY OF THE INVENTION

A measuring device, such as a heart rate monitor, or a pulse oximeter, may be a transmissive or a reflective device. A transmissive measuring device may measure a set of lights that has travelled through a predetermined part of the user's body, and a reflective measuring device may measure a set of lights reflected by a predetermined part of the user's body.

Existence of such different types of measuring devices, however, create significant challenges in testing the measuring device itself.

Frequently, a tester device is employed to test each measuring device, such as by the manufacturer, or in the field such as by the hospital, to ensure that they are operating acceptably. In turn, each tester device must be ensured to be working acceptably so that they can test each measuring device.

The performance of the tester device may be tested with a reference device. A reference device, also referred to as a "golden unit", may be configured similarly to a measuring device but with known performance characteristics. The tester is validated using a configuration that is a reverse of a measuring device test. To validate a transmissive tester (tester device for transmissive measuring devices), a transmissive golden unit may be coupled to the tester, whereas a reflective reference device may be coupled to the tester to validate a reflective tester (tester device for reflective measuring devices).

For example, the tester will be determined as acceptable if the measurement result of the golden unit with tester is within acceptable predetermined range. This may make the tester device eligible to be used for device testing.

Thus, the reference device must be the same configuration as the measuring device to be tested. To this end the manufacturer of a measuring device must acquire or develop a compatible reference device of the same configuration as the measuring device must be acquired (or developed), or limit development of the measuring device to be compatible with the array of available reference devices.

This may add inconvenience, time, and overall cost to the measuring device manufacturer. Furthermore, a reference device may be limited in range, and in turn limit development of measuring devices, stifling innovation and technology development to the detriment of healthcare professionals and/or users.

Thus, the present technology contemplates a tester device operable in a plurality of configurations, for example to be validated by a reference device of a first configuration (e.g. transmissive) and test a measuring device of a second configuration (e.g. reflective).

In other words, the tester device may be operable in a plurality of test modes, such that in each test mode the tester device is capable of testing a measuring device of a different configuration. Conversely, the tester device may be able to be tested by a plurality of reference device types.

Such a tester device according to aspects of the present technology may advantageously be able to test multiple configurations of measuring devices in the field, saving cost and valuable space in factories of hospital settings. It may also free up the manufacturer from designing measuring devices that have substantially the same configuration as existing reference devices. Additionally, such a tester device may allow use of a reference device of a different measurement configuration to the measuring device. These advantages ultimately leading to mitigating or ameliorating the aforementioned challenges in the field.

According to one aspect, the present technology comprises a tester device for testing a measuring device, the tester comprising a first light detector set and a second light detector set, wherein each light detector set is configured to detect light received thereonto and generate a signal indicative of the detected light; a light emitter set for outputting light; and a processor configured to receive and analyse the signal to identify presence of a first set of predetermined wavelengths in the detected light, wherein the processor is further configured to trigger the light emitter set to begin outputting light at a second set of predetermined wavelengths if at least one of the first and second light detector set is determined to have received light containing the first set of predetermined wavelengths.

According to one aspect, the first light detector set may be located on a first side of the tester device and the second light detector set is located on a second side of the tester device, and the first and second sides substantially oppose each other.

According to one aspect, the tester device may further comprise a tester rod including the first side and the second side.

According to one aspect, the tester rod may further comprise an optical isolator comprising a protrusion configured to reduce light leakage between the light emitter set and the second light detector set.

According to one aspect, the optical isolator may be compliant to assist in forming an optical seal between itself and the measuring device upon contact.

According to one aspect, the optical isolator may be constructed from at least one of: a foam material, silicone or thermoplastic elastomer.

According to one aspect, the optical isolator may further comprise a device mount configured to receive the measuring device and movable between a first position to locate the measuring device for testing, and a second position to allow the measuring device to be removed from the device mount.

According to one aspect, the device mount may be biased to urge the measuring device towards the first position.

According to one aspect, the device mount may be slidable along a base of the test device.

According to one aspect, the device mount may be movable along a direction at an angle between 20 and 60 degrees to a direction of light from the light emitter set.

According to one aspect, the device mount may comprise a cavity configured to receive a portion of the measuring device.

According to one aspect, the tester device may further comprise a connector for electrical communication with the measuring device.

According to one aspect, the tester device may be configured to provide power to and/or receive a signal from the measuring device through the connector.

According to one aspect, the tester device may be configured to receive signal from the measuring device to determine an outcome of a test for the measuring device.

According to one aspect, the device mount may be movable to a third position to receive a second measuring device.

According to one aspect, the first set of predetermined wavelengths may comprise a first wavelength between 600 nm-750 nm and a second wavelength between 850 nm-1000 nm.

Another form of the present technology relates to a tester device for testing an optical measuring device, the tester device comprising a light emitter set for emitting a set of lights to the optical measuring device; and a plurality of light detector sets, each set of light detectors configured to receive a set of lights from the optical measuring device, wherein the tester device is operable in a plurality of modes to test optical measuring devices and in each of the plurality of modes the tester device is configured to test an optical measuring device with the light emitter set and one of the plurality of light detector sets to test the optical measuring device.

According to one aspect, the tester device may be configured to test a transmissive pulse oximeter in a first mode and configured to test a reflective pulse oximeter in a second mode.

BRIEF DESCRIPTION OF THE DRAWINGS

A more complete understanding of the present invention may be derived from the following detailed description of exemplary embodiments thereof and claims when considered in conjunction with the following figures, wherein like reference numbers refer to similar elements throughout the figures, which may be illustrated for simplicity and clarity and are not necessarily drawn to scale, in which:

FIG. 13 shows a simplified side-on schematic view of the tester device as shown in FIG. 11, showing the device mount placed away from the tester rod.

FIG. 14 shows the tester device as shown in FIG. 13, showing the device mount placed adjacent the tester rod for testing.

DETAILED DESCRIPTION

Reference will now be made in detail to the embodiments of the present invention. While the invention will be described in conjunction with these embodiments, it is envisaged that alternatives, modifications and equivalents would be feasible while still remaining within the spirit and scope of the invention as defined by the appended claims.

Furthermore, in the following detailed description of the present invention, numerous specific details are set forth in order to provide a thorough understanding of the present invention. However, it will be understood that the description is merely illustrative and is not intended to limit embodiments and/or application or uses of embodiments. On the contrary, the present invention may be practiced without these specific details in various cases. In some instances, well known methods, procedures, components, and circuits have not been described in detail to not unnecessarily obscure aspects of the present invention.

The term "user" as used throughout this specification is not to be limited to those who is operating a device, such as a measuring device. "User" may include any person whose physiological parameter is being measured, even if another person is operating the measuring device.

Unless otherwise specified, Figure reference labels with similar suffixes may have similar functions across different Figures.

Figure 1:
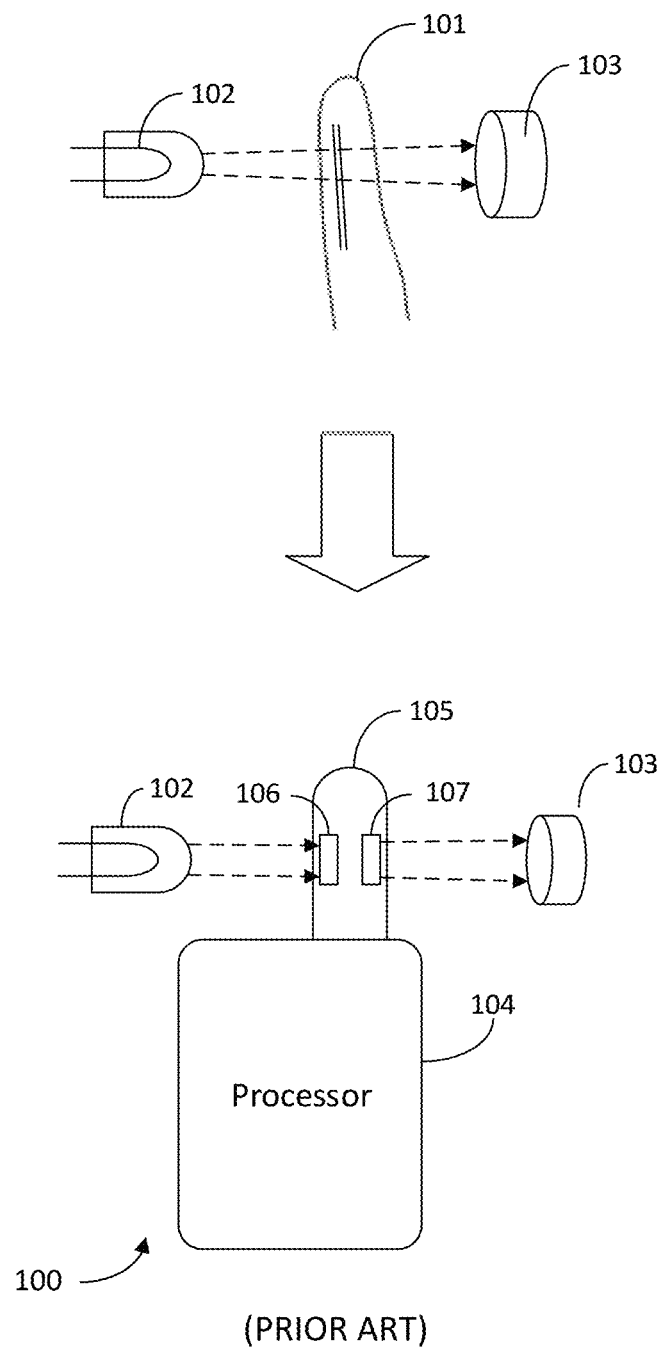
FIG. 1 shows an example schematic of a prior art tester for testing a transmissive measuring device.
Figure 2:
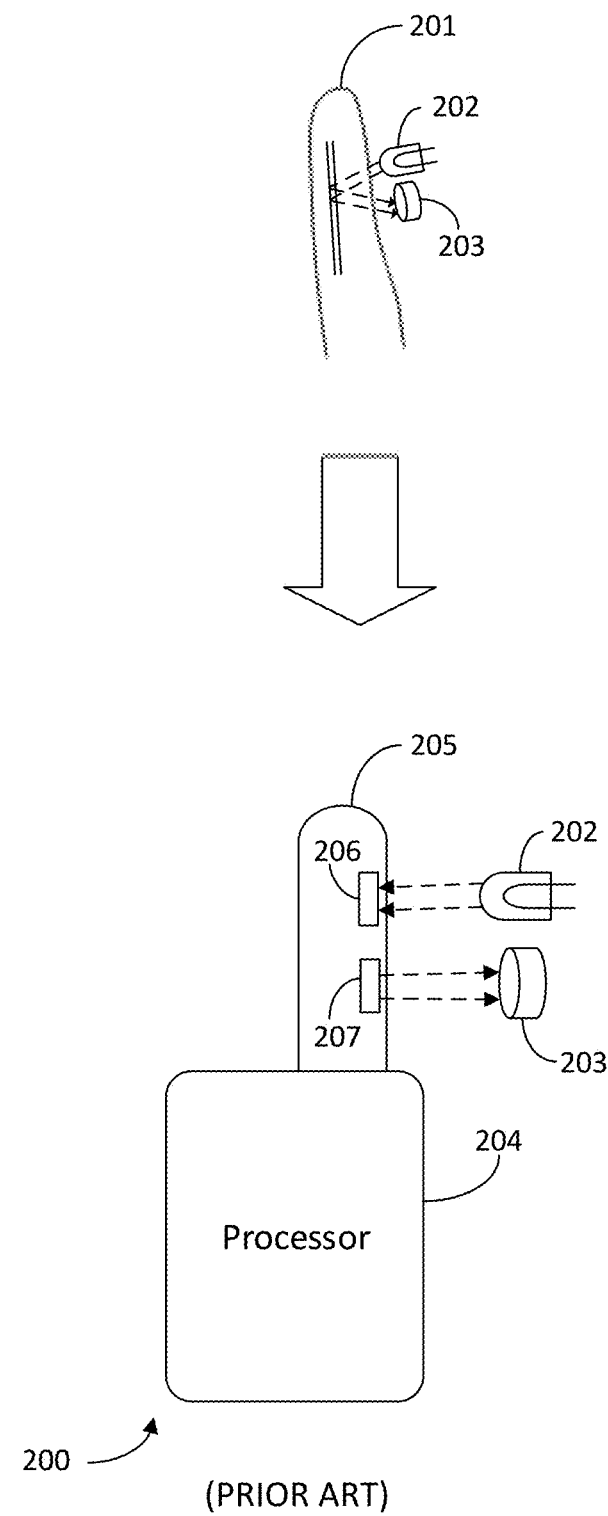
FIG. 2 shows an example schematic of a prior art tester for testing a reflective measuring device.

FIG. 1 and FIG. 2 respectively show example schematics of prior art optical transmissive and reflective measuring devices and corresponding tester devices, or testers, for testing the respective measuring device.

FIG. 1 shows a transmissive optical measuring device, e.g., a pulse oximeter. As described before, the measuring device comprises a set of light emitters (measuring emitter set) and a set of light detectors (measuring detector set), and is configured to determined blood oxygen saturation and/or other physiological parameters such as a heart rate of the user.

To test the measuring device, a tester 100 may be placed between the set measuring emitter set 102 and the measuring detector set 103 as shown in the bottom half of FIG. 1. The tester device 100 simulates the digit 101 by outputting a set of lights (tester lights) to the set of measuring detectors 103, for example at predetermined parameters or correlated to the set of lights from the set of measuring emitters 102.

The tester 100 may comprise a set of light detectors (tester detector set) 106 and a set of lights emitter (tester emitter set) 107 on the tester body 105 as shown in FIG. 1. The tester detector set 106 may be located to receive light emitted from the measuring emitter set 102 and a tester emitter set 107 may be located to output a set of light to the measuring detector set 103.

The tester emitter set 107 may comprise a set of light emitting diodes (LEDs) configured to deliver light at a first frequency (e.g. 600 nm-750 nm) and light at a second frequency (e.g. 850 nm-1000 nm), and the tester detector set 106 may comprise a set of photodetectors (PDs) configured to detect light at the first and the second frequencies.

Furthermore, the tester device 100 may further comprise, or be coupled to, a processor 104 operable to analyse the light detected by the tester detector set 106 and control the tester emitter set 107.

The processor 104 may be configured to receive signals from the tester detector set 106 indicative of the light received, and identify presence of predetermined wavelengths and/or their intensities. The processor 104 may thus determine when the measuring device has commenced measurement, and trigger the tester emitter set 107 accordingly to simulate light returning from the user to the measuring device.

For example, the tester emitter set 107 may generate a set of lights expected to be received from a user with a predetermined blood oxygen saturation (SpO2) value. Thus, if the measuring device infers a SpO2 value within a margin of error of the predetermined SpO2 value, the measuring device may be deemed to have passed the test. The set of lights from the tester emitter set may comprise a set of wavelengths which may be identical to, or based on, the one or more wavelengths in the light received.

In another form as shown in FIG. 2, a reflective optical measuring device includes a set of measuring emitters 202 and a set of measuring detectors 203. A reflective optical measuring device, in contrast with the transmissive optical measuring device, is configured to measure a set of lights reflected from the digit 201 rather than transmitted therethrough.

A tester device 200 configured to test a reflective measuring device may comprise a tester body 205 comprising a set of tester detectors 206 and a set of tester emitters 207. A processor 204 of the tester 200 may process a set of signals indicative of the set of lights received by the set of tester detectors 206 and control the set of tester emitters 207 to generate a set of lights and perform a test as previously described.

As described previously, a reference device may be used for a task of validating the tester device's performance.

Figure 10:
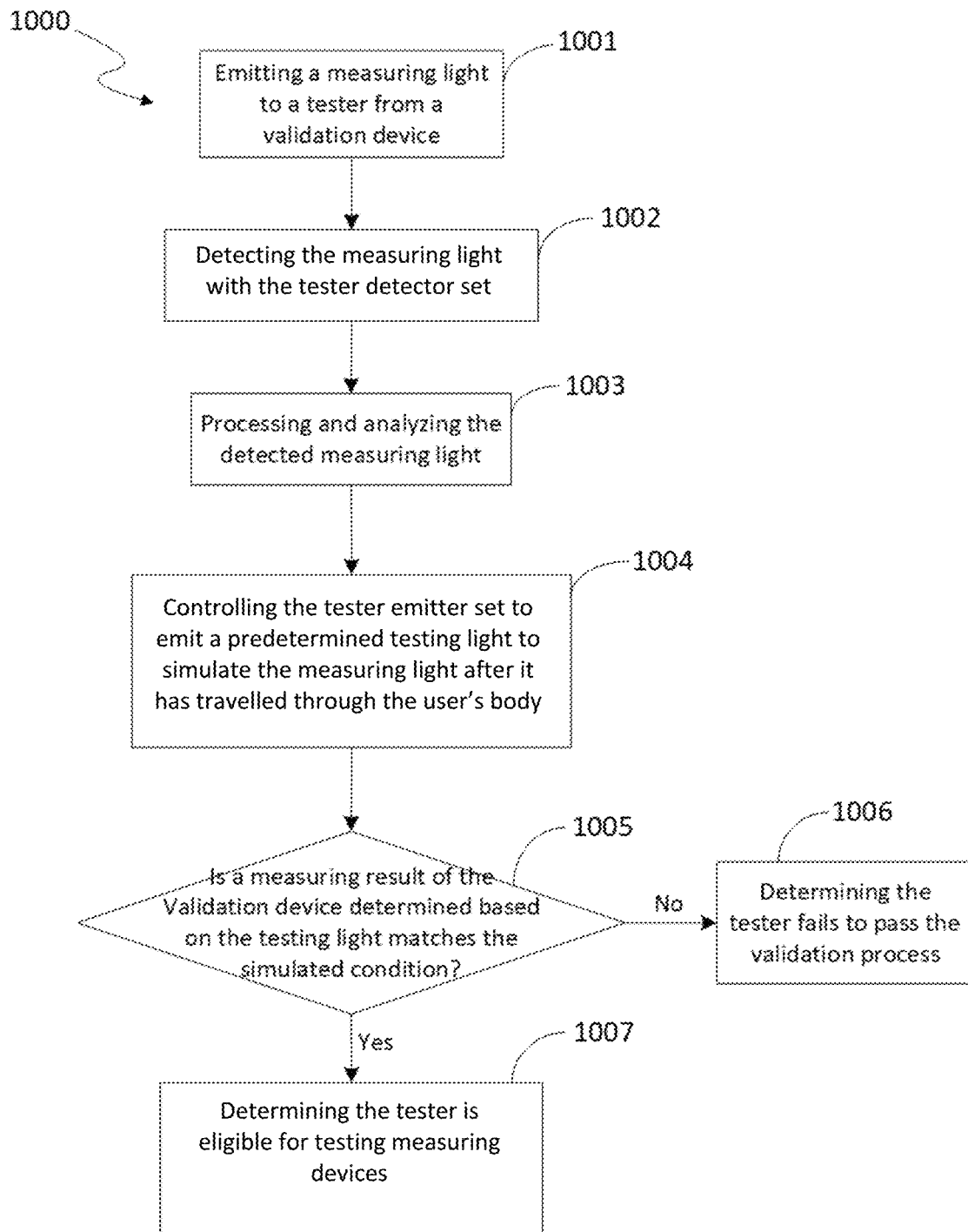
FIG. 10 shows a flowchart illustrating an example validation method for a tester device.

FIG. 10 shows a flowchart 1000 of an example validation method for a tester device. When a reference device emits a measuring light to the tester, in step 1001, the tester detects the measuring light via a tester detector set in step 1002. After processing and analysing the detected measuring light in step 1003, the tester controls a set of emitters to emit a predetermined testing light to the reference device in step 1004 at a set of parameters to simulate a real condition of the measuring light as though it has travelled through a user's body. If a measured physiological parameter determined by the reference device based on the testing light matches the simulated condition in step 1005, the tester is determined as eligible for testing measuring devices in step 1007. Otherwise, the tester is determined as failing to pass the validation process in 1006.

It will be then understood from the foregoing description that relative positioning of the sets of emitters and detectors are important.

It can also be seen that a transmissive measuring device and a reflective measuring device are geometrically incompatible. In fact, two measuring devices of the same type may not be compatible with one tester device depending on their geometry, for instance.

In some forms, each light emitter may comprise a light emitting diode (LED) of 2-10 mm diameter or side length, such as 3, 5, or 7 mm. The relatively small sizes may mean that for example, two different reflective measuring devices may not both be compatible with a tester device, if the arrangement of the set of emitters and the set of detectors between the two measuring devices are sufficiently different to each other.

The same problem may limit a design or arrangement of a measuring device to an available array of reference devices in the market. If a reference device of a particular configuration cannot be found, a manufacturer of measuring devices may be put into a bind as they may encounter a problem in either testing or measuring.

Thus, one aspect of the present technology relates to a tester device that is compatible with multiple configurations of a measuring device, to enable use with a measuring device of a first configuration and a reference device of a second configuration (or vice versa).

Figure 3:
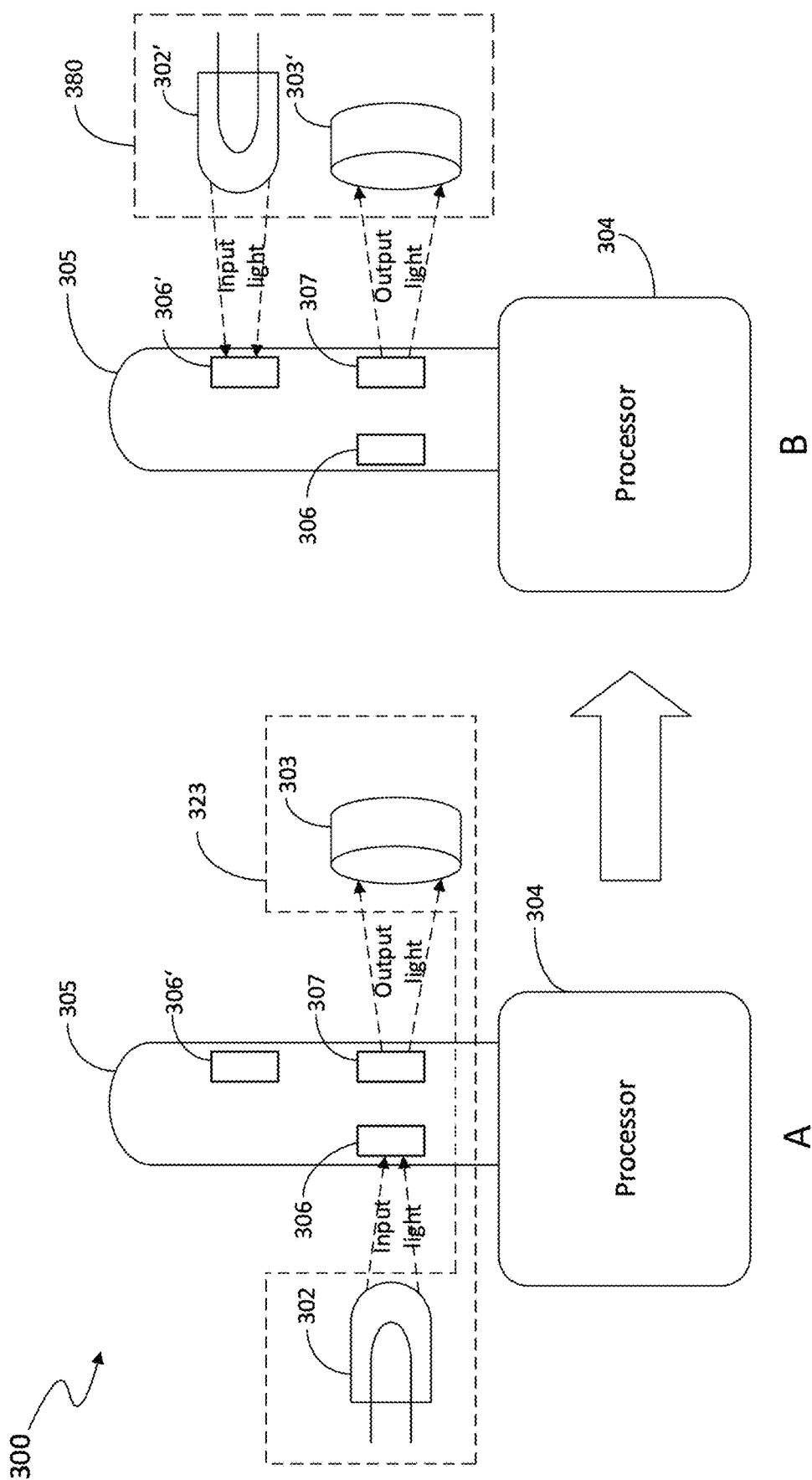
FIG. 3 shows a tester in accordance with one embodiment of the present invention.

FIG. 3 shows a schematic drawing of a tester device 300 for testing transmissive and reflective devices in accordance with one embodiment of the present invention. As shown in FIG. 3, the tester 300 comprises a first tester detector set 306, a second tester detector set 306' and a tester emitter set 307. The first tester detector set 306 and the tester emitter set 307 are arranged to face opposing directions to accommodate a transmissive measuring device 323, while the second tester detector set 306' and the tester emitter set 307 are arranged to face the same side to accommodate a reflective measuring device 380.

The tester device 300 may further comprise a processor 304 for signal processing and control.

During operation, the processor 304 may communicate with a tester detector set (306 or 306') and the tester emitter set 307 to synchronize the operation therebetween to accurately simulate an in-vivo measurement.

For instance, the tester device 300 may be configured to react to one or more triggering events before outputting a set of lights from the set of tester emitters 307.

In one embodiment, the tester device 300 may be configured be triggered based on a signal from a tester detector set indicative of received lights, by one or more of: detection of any light from a measuring device, the intensity of the detected light being above a predetermined threshold, the intensity of the detected light increasing by an amount greater than a predetermined threshold, or the intensity of the detected light being higher than a predetermined threshold for a predetermined period of time. Any number of other triggering mechanisms may be also suitable.

Upon triggering, the tester device 300 may output a corresponding set of lights back to the measuring device 323 to approximate light from the user during an in-vivo measurement, for example based on the detected light from the measuring device.

The set of lights output by the tester device 300 may correspond to an SpO2 value, for example according to a predetermined table from a readable storage medium.

Advantageously, the tester device 300 of FIG. 3 may allow triggering of the tester emitter set 307 to occur from either of the plurality of tester detector sets 306 and 306'. Accordingly, the tester device 300 may be compatible with both of a transmissive measuring device and a reflective measuring device.

Advantageously, using only one set of emitters 307 in both configurations, ensures that the performance of the tester device 300 remains consistent for both configurations.

FIG. 3 shows that in the transmissive configuration (configuration A), the first tester detector set 306 is configured to receive a set of lights from a measuring emitter set 302, whereas in the reflective configuration (configuration B), the second tester detector set 306' is configured to receive a set of lights from another set of measuring emitters 302'. In both configurations, the tester emitter set 307 is used to output a set of lights to a set of measuring detectors 303' of the subject measuring device.

Upon triggering, the processor 304 will analyse the signal indicative of the detected set of lights to determine one or more attributes of the measured set of lights, e.g. wavelengths of the set of lights. The determined attributes may form inputs for the processor 304 in controlling the set of tester emitters 307 to output a set of testing lights to the measuring device. Thus, the set of tester emitters 307 may deliver a set of testing lights comprising the measured wavelengths. In some forms, the set of testing lights may comprise a set of predetermined wavelengths corresponding to the set of detected wavelengths, such as from a lookup table.

One or more parameters of the set of testing lights output from the set of testing emitters 307 may be predetermined, for example to test a particular physiological parameter. The tester 300 may be configured to test one or more types of measuring devices, such as a pulse oximeter or a heart rate monitor.

In one embodiment, the set of testing lights comprises one or more wavelengths corresponding to those emitted from the set of measuring emitters 302, and/or wavelengths corresponding to one or more physical parameters to be measured. The intensities of the set of testing lights may also be predetermined based on the physiological parameter, so as to simulate an in-vivo measurement.

According to aspects of the present invention, the tester device comprises a plurality of tester detector sets (such as 306 or 306'), only one of which is used to trigger the tester device.

At the same time, other components including the processor 304 and the tester emitter set 307 are used in each testing mode. This allows the tester device to output a set of tester lights output consistently and accurately in each of a plurality of testing modes. Under such condition, if the tester 300 is determined to be eligible for performing device testing on the transmissive measuring devices, the tester 300 will be regarded as also being eligible to perform device testing on the reflective measuring devices. The reason being that critical components as the light emitting unit 307 and the processor 304 are re-used in each testing configuration.

In other words, the present technologies advantageously allow a tester device (e.g. 300) to be validated using one type of reference device (e.g. transmissive reference device), while still allowing it to test measuring device of a different type to that used to validate the tester device.

As such, once the tester 300 passes the validation process with a transmissive golden unit, it may be advantageously also accredited to perform device testing on the reflective measuring devices, and vice-versa.

The arrow between configurations A and B in FIG. 3 will be understood as indicative of different, reversible, configurations. It will also be understood that other embodiments in this document will have similar reversible configurations.

Figure 4:
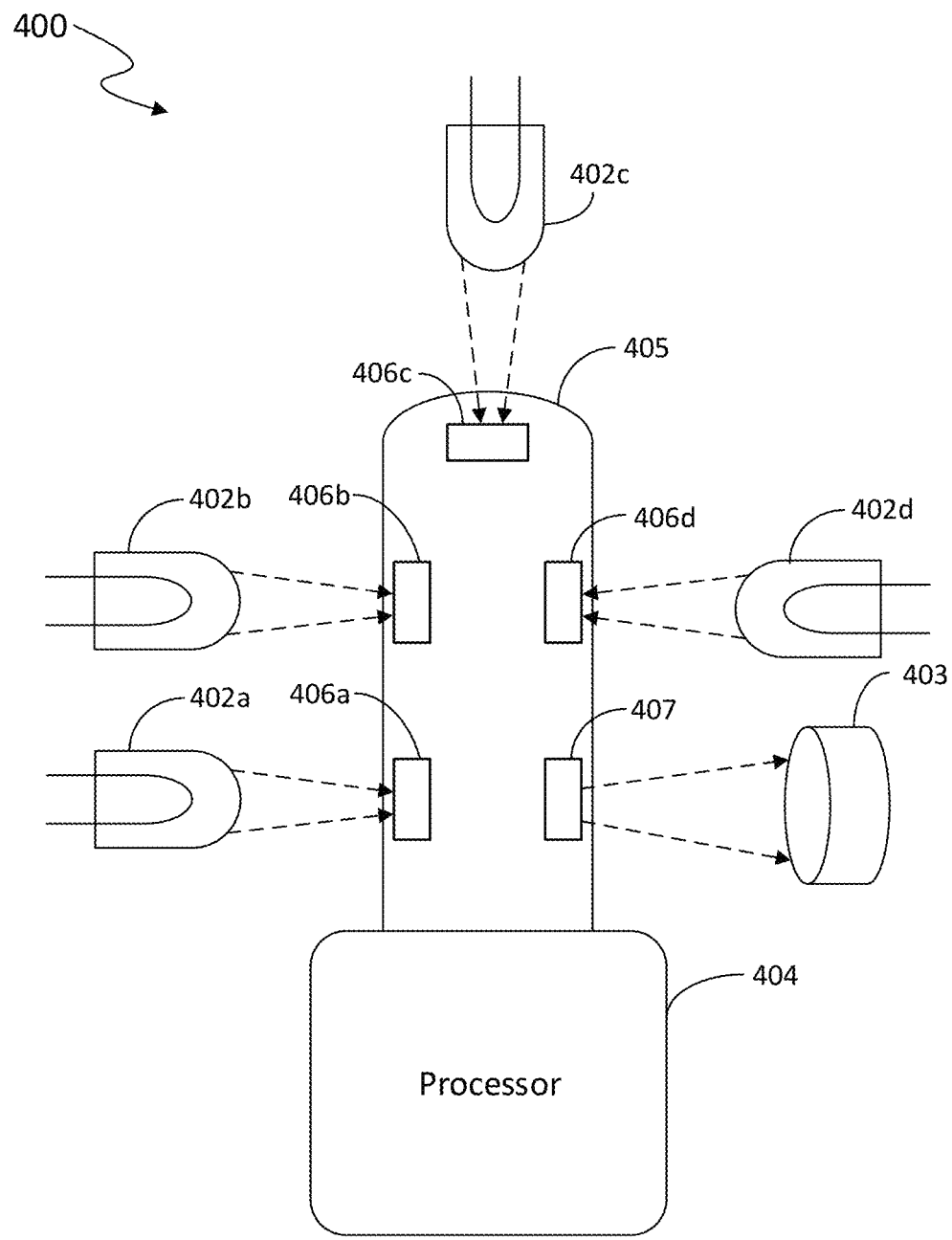
FIG. 4 shows a tester in accordance with another embodiment of the present invention, comprising a plurality of tester detector sets.

In some embodiments, a tester may comprise further sets of tester detectors for testing additional types or arrangements of measuring devices. FIG. 4 shows a tester device 400 configured to test a plurality of arrangements of measuring devices, in accordance with another embodiment of the present invention.

In FIG. 4, the tester 400 comprises four tester detector sets 406a-406d arranged at different positions of a tester body 405 for detecting measuring light incident from different directions, and/or from different locations. Each of the tester detector sets 406a-406d is in communication with the processor 404 to trigger the tester emitter set 407. Otherwise put, any of the plurality of sets of tester detectors 406a-406d can, together with the tester emitter set 407, test a measuring device or be used for validation of the tester device.

In one example, a set of tester detectors 406a, a set of tester emitters 407 and the processor 404 are operable to test a transmissive measuring device comprising a measuring emitter set 402a and a measuring detector set 403. In this arrangement, the tester detector set comprises a first normal direction, to the left of the figure, and the tester emitter set comprises a second normal direction, to the right of the figure and in an opposing direction to the first normal direction.

In another example, a tester detector set 406d, a tester emitter set 407 and the processor 404 are operable to test a reflective measuring device comprising a measuring emitter set 402d and a measuring detector set 403 arranged on the same side. In this arrangement, a normal of the tester detector set and a normal of the tester emitter set are parallel and offset to each other.

In a yet another example, a tester detector set 406b, a tester emitter set 407 and the processor 404 are operable to test trans-reflective measuring devices comprising a set of measuring emitters (e.g. 402b or 402c) and a measuring detector set 403 as shown. In these configurations (i.e. in a trans-reflective testing mode), the tester detector set 406b or 406c not only face a different direction to the tester emitter set 407, but their normal directions are also not co-axial with each other.

Thus, the set of tester emitters 407 and the processor 404 are able to be used in a plurality of testing modes, e.g., the transmissive testing mode, the reflective testing mode and/or trans-reflective testing mode. By validating the tester in one of the plurality of testing modes, the tester could be used in each of the remainder of the plurality of testing modes, to test various arrangements of measuring devices, increasing flexibility of the validation on the tester as well as its utility.

It will be understood that the configuration of the tester body 405 is not limited to the embodiment as shown in FIG. 4. For instance, the plurality of sets of tester detectors 406a-406d may be placed at a myriad other locations or directions with respect to each other, as well as having more or fewer sets of tester detectors than what is shown.

Figure 5:
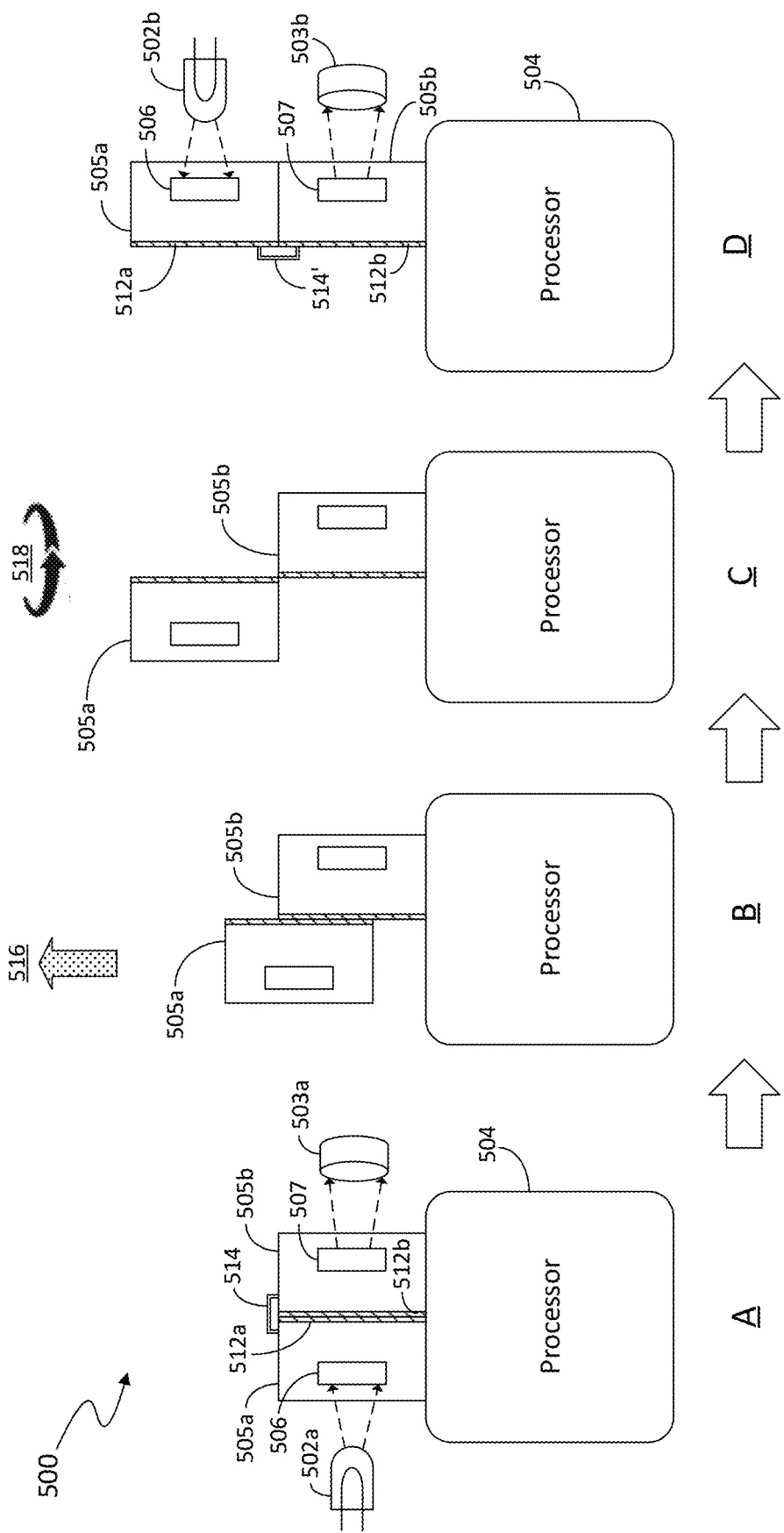
FIG. 5 shows a tester in accordance with another embodiment of the present invention, comprising a movable body.

FIG. 5 shows another tester device 500 configured to test multiple configurations of measuring devices, in accordance with another embodiment of the present invention. The tester 500 comprises a first tester body 505a comprising a tester detector set 506 and a second tester body 505b comprising a tester emitter set 507, where the first tester body 505a is moveable in relative to the second tester body 505b.

In this embodiment, the first and second tester bodies may be movable relative to each other to form a plurality of testing configurations. In a first configuration (configuration A in FIG. 5), the tester bodies 505a and 505b are placed such that the light detecting unit 506 and the light emitting unit 507 are in line with each other facing opposite directions to couple with a transmissive measuring device, or a reference device including a set of measuring emitters 502a and a set of measuring detectors 503a.

Optionally, the tester device 500 may further comprise a locking component 514 operable to lock the tester body 505a in position relative to the tester body 505b.

The tester device may be transformable to another configuration (e.g. configuration D) in order to couple with a (e.g. reflective) measuring device of a different configuration. Configurations B and C of FIG. 5 show intermediary steps for one such example transformation.

The tester body 505a may be slidable (e.g. along 516) and rotatable (e.g. along 518) until the set of tester detectors 506 and the set of tester emitters 507 face the same direction and tester device is optically coupled with a reflective measuring device. The tester device 500 may further comprise a lock 514' for locking the bodies 505a and 505b.

The tester body 505a may be moved and/or rotated with respect to the tester body 505b, e.g., as shown in stage B or stage C, or in any other position, to suit a particular measuring device as required.

Figure 6A:
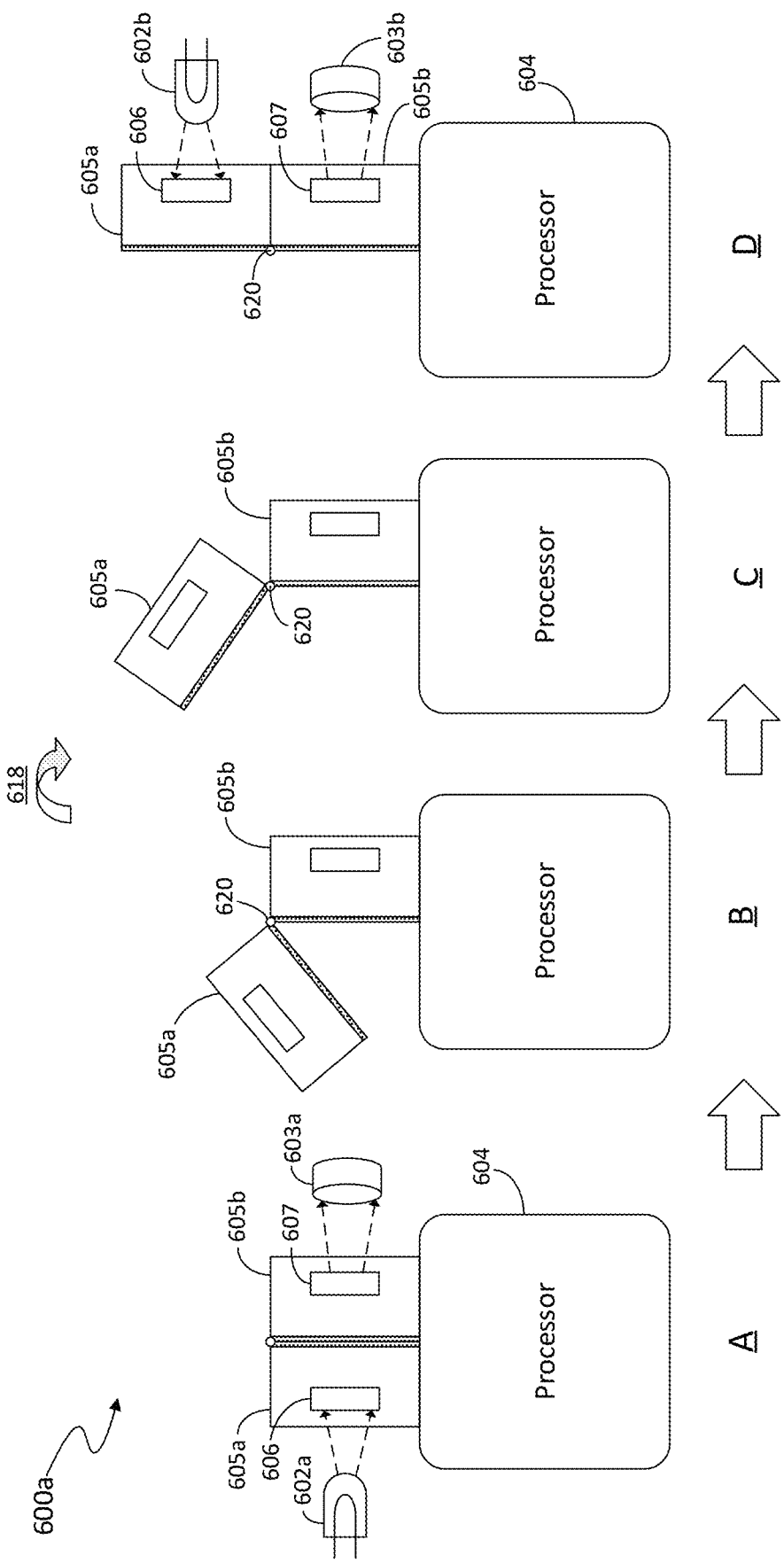
FIG. 6A shows a tester in accordance with another embodiment of the present invention, comprising a movable body.
Figure 6B:
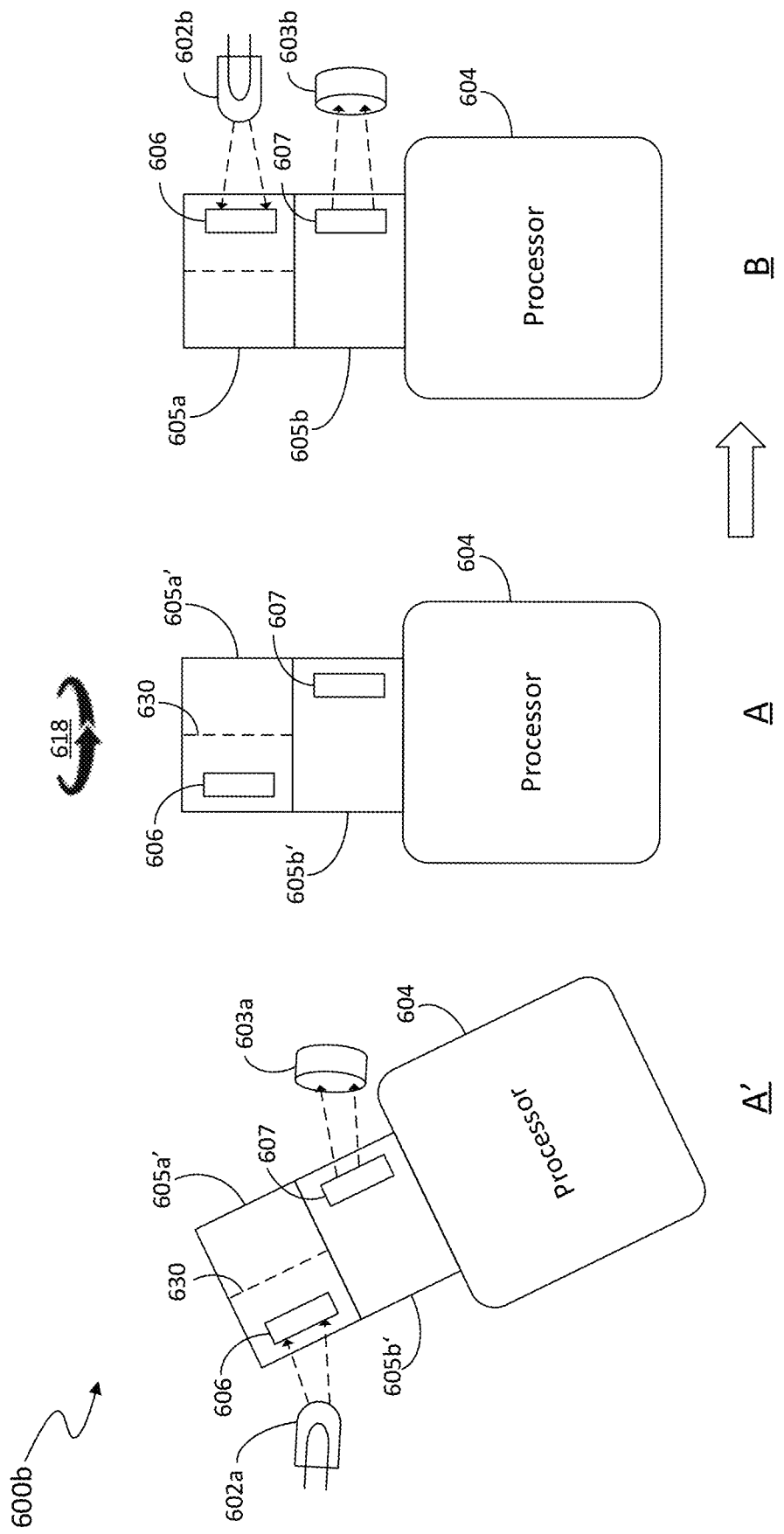
FIG. 6B shows a tester in accordance with another embodiment of the present invention, comprising a movable body.

FIGS. 6A and 6B show testers 600a and 600b respectively configured to test a plurality of configurations of measuring devices, in accordance with another embodiment of the present invention.

In one embodiment, as shown in FIG. 6A, the tester 600a comprises a tester body 605a configured to rotate about an axis 620 with respect to a fixed tester body 605b in a direction as indicated by an arrow 618 to align a set of tester detectors 606 and a set of tester emitters 607 with a measuring device. The tester 600a as shown could be in a first configuration (configuration A) for testing a transmissive measuring device, and also in second configuration (configuration B) for optically coupling with a reflective measuring device.

In an alternative embodiment, as shown in FIG. 6B, the tester device 600b may comprise a tester body 605a' rotatable along an axis 630, such as in a direction as indicated by an arrow 618. The tester 600b could be in a first configuration (configuration A') to test a transmissive measuring device as shown in stage A' by configuring the tester 600b as shown in between a measuring emitter set 602a' and a measuring detector set 603a' of the subject measuring device, and further be configured to test a reflective measuring device as shown in stage B by positioning the tester 600b besides a measuring emitter set 602b and a measuring detector set 603b of the subject measuring device.

Figure 7:
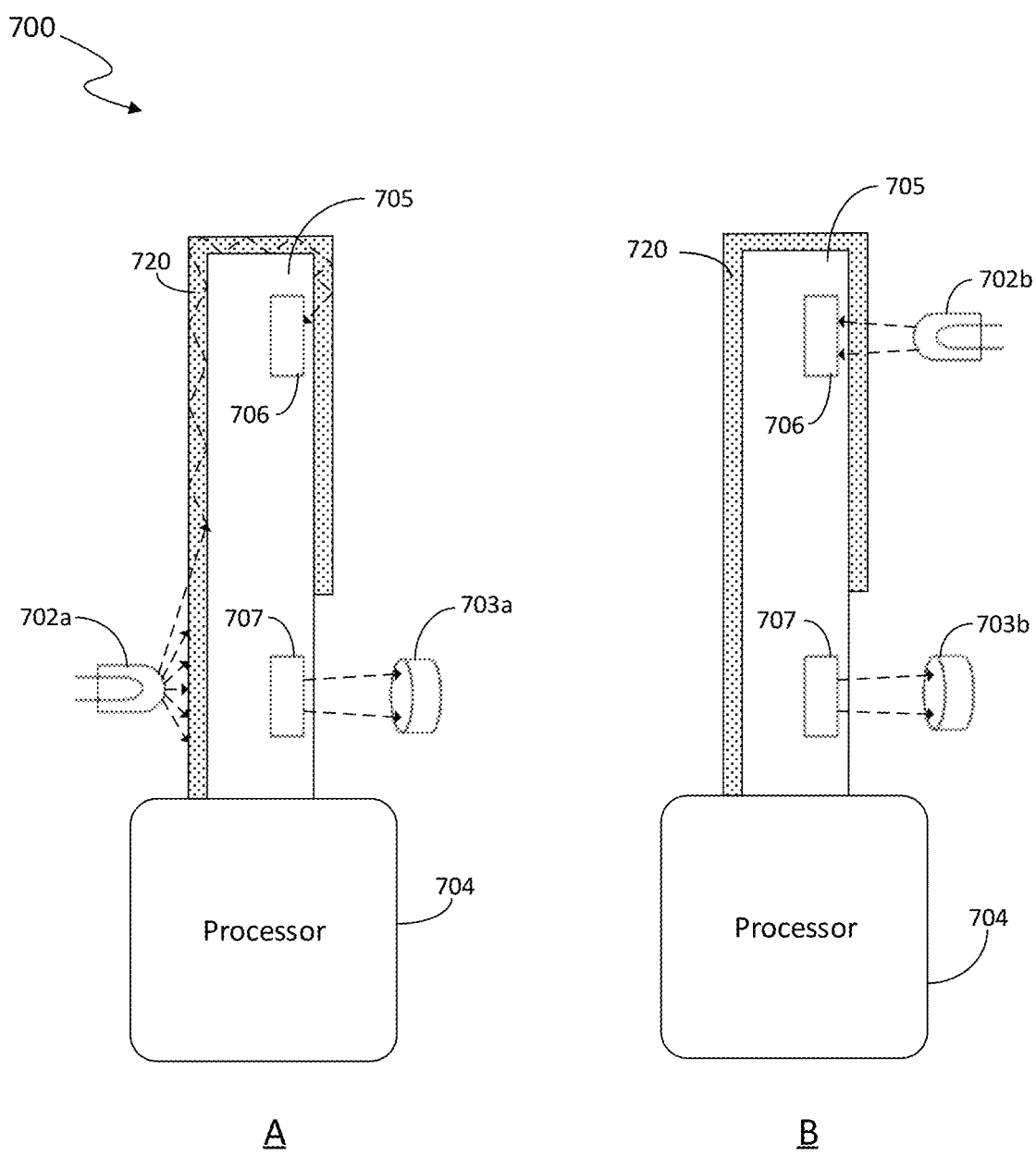
FIG. 7 shows a tester in accordance with another embodiment of the present invention, comprising a light guide.

FIG. 7 shows a tester device 700 in accordance with another embodiment of the present invention. In FIG. 7, the tester 700 comprises a tester body 705 comprising a tester detector set 706 and a tester emitter set 707. The tester device further comprises a light guide 720 configured to deliver a portion of a received light thereto a target location.

The light guide 720 is located on the tester body 705 and configured to guide a light from a measuring emitter set 702a corresponding to a measuring detector set 703a of a transmissive measuring device. Thus, the light guide extends from a first location to a second location to deliver light received at the first location to the tester receiver set 706 at the second location, where the first location is behind and axially in line with the tester emitter set 707 and the set of lights to be emitted therefrom.

The light guide 720 may guide the received light from the first location to the second location by internal reflection, as indicated by an arrow path within the light guiding unit 720.

In one embodiment, the light guide 720 comprises a set of lenses. The set of lenses may comprise surfaces plated with light-reflective material. In some forms, the light reflecting material may extend from an end of an opening for receiving the light into the light guide 720, to an outlet for the light guide 720.

Accordingly, a transmissive reference device may be optically coupled with the tester 700 by optically coupling a set of reference detector 703a with a tester emitter set 707 and optically coupling a set of reference emitters 702a with the light guide 720, such as in line with and at an opposing side of the light detector 702a for emitting a set of reference lights to the tester 700. Thus, light from the set of reference emitters 702a is received and guided by the light guide 720 to the set of tester detectors 706. The tester detector set 706 may be in communication with the processor 704 to process and analyse the detected light, for example to trigger the tester emitter set 707 according to the analysis.

Figure 8:
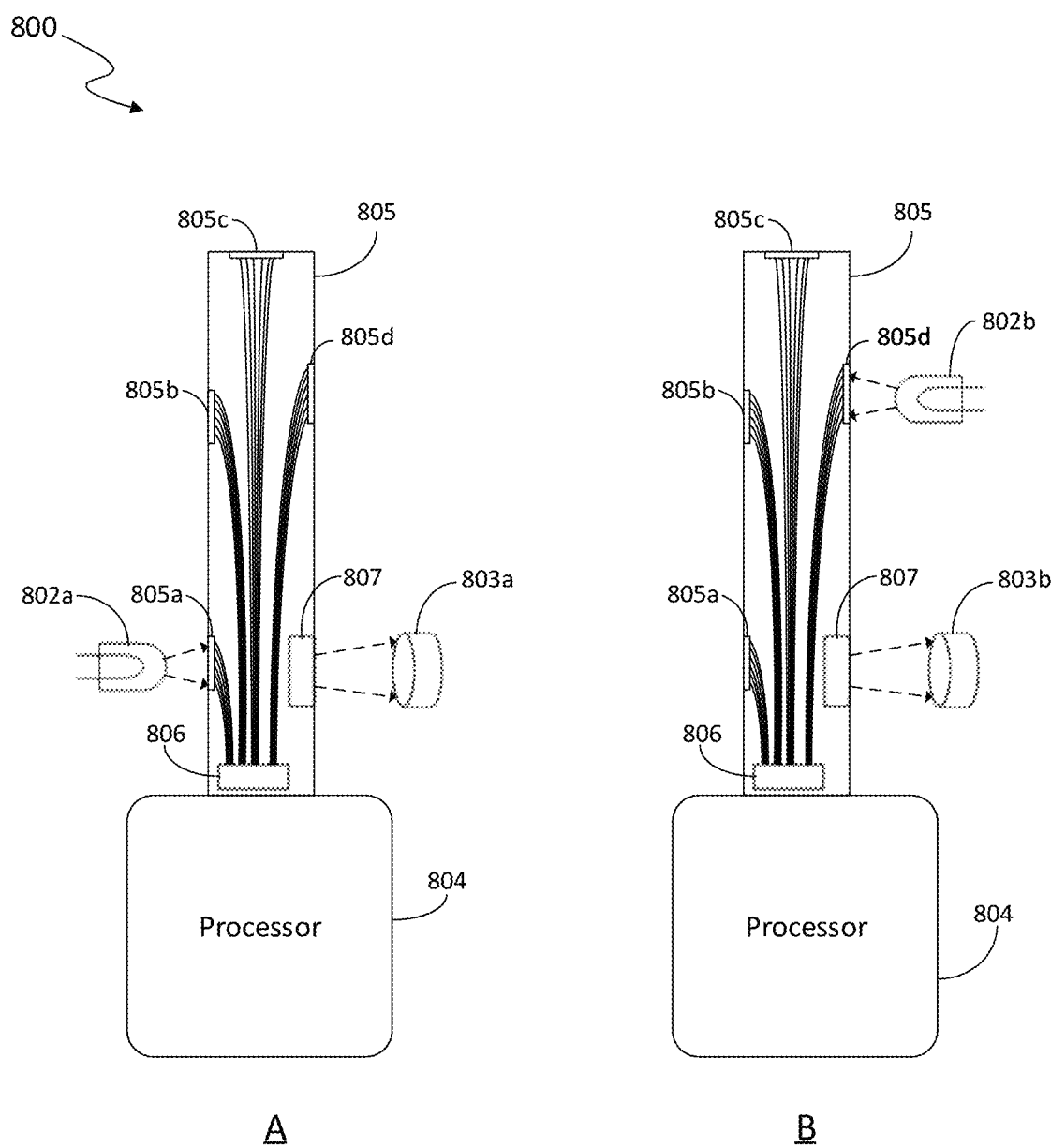
FIG. 8 shows a tester in accordance with another embodiment of the present invention, comprising a set of windows optically connected to a tester detector set.

FIG. 8 shows a tester device 800 in accordance with another embodiment of the present invention. The tester 800 comprises a tester body comprising a tester emitter set 807, a tester detector set 806 and a plurality of windows 805a-d for receiving light incident from different directions. The tester device further comprises a plurality of sets of optical fibre for transmitting light from the window unit to the tester detector set 806.

Similar to the configuration shown in FIG. 4, the tester device 800 of FIG. 8 is configured to detect light received at any of the plurality of windows 805a-d and to trigger the tester emitter set 807.

Figure 9:
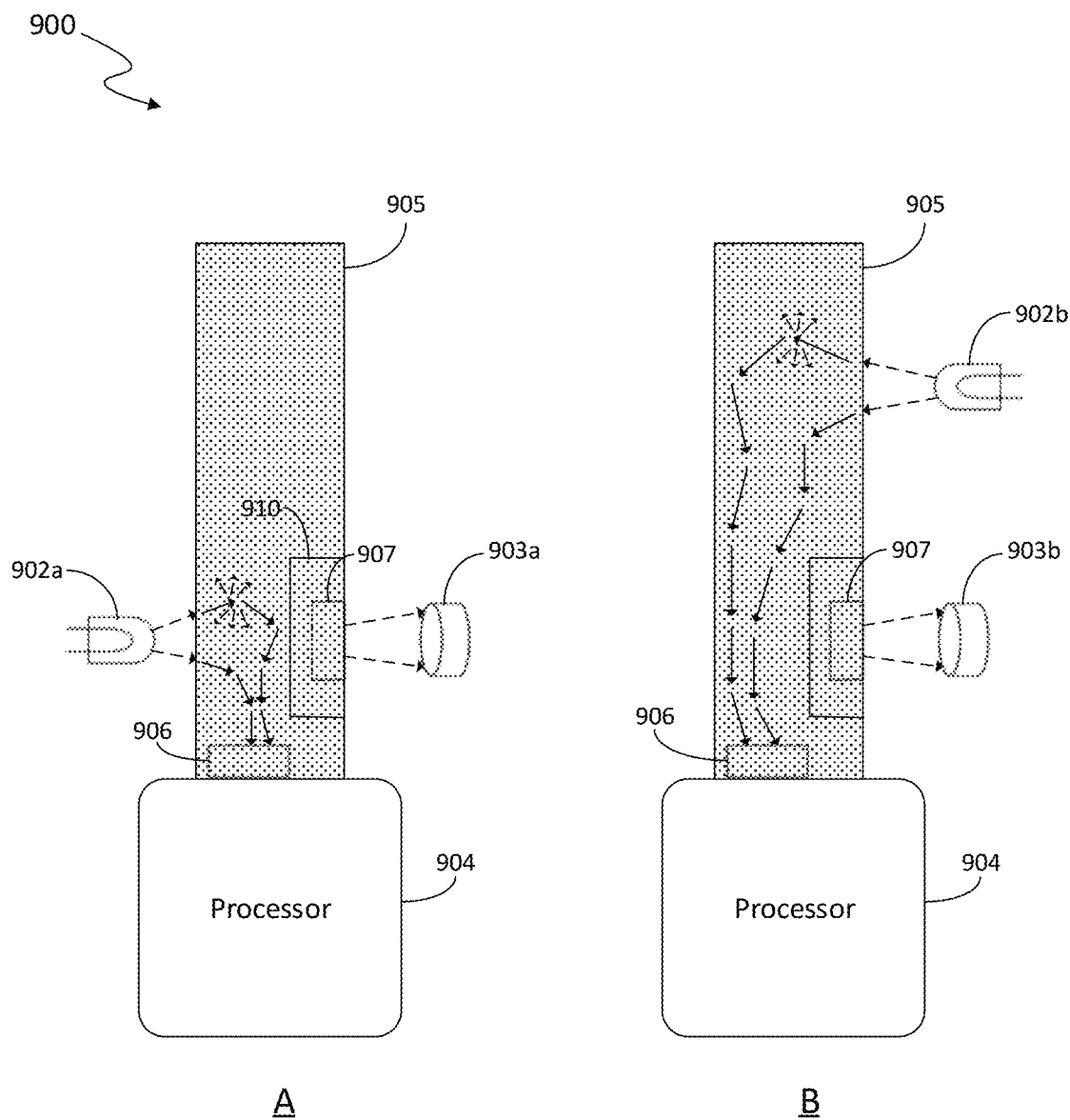
FIG. 9 shows a tester in accordance with another embodiment of the present invention, comprising a tester body including light scattering materials.

FIG. 9 shows a tester device 900 comprising a tester emitter set 907, a tester detector set 906, and a tester body 905 configured to diffuse light therein to deliver light incident upon one or more locations on the tester body 905 to the tester detector set 906. In one embodiment, the tester body 905 comprises scattering materials for scattering light within the body. The tester body may comprise an optical isolation layer 910 to isolate the set of tester emitters 907 from the light within the tester body 905 such that light from the set of tester emitters 907 is not contaminated.

In use, light from an emitter set 902a of a transmissive measuring device or a reference device may enter the tester body 905. The light may be scattered by the scattering materials within the tester body, causing some of it to arrive at the tester detectors 906, as illustrated in configuration A of FIG. 9. The tester detector set 906 may detect the light and accordingly trigger the set of tester emitters 907. Similarly, light from a set of emitters 902b of a reflective measuring device or reference device may reach the tester detector set 906 through internal scattering.

Once a portion of the light reaches the tester detector set 906, the processor 904 may trigger the tester emitter set 907 similarly to above.

FIGS. 11-14 show another embodiment of the present invention, showing a tester device 1100 comprising a tester body 1105, a processor 1104, a device mount 1110, a first tester detector set 1106a, a second detector set 1106b and a tester emitter set 1107.

Figure 11:
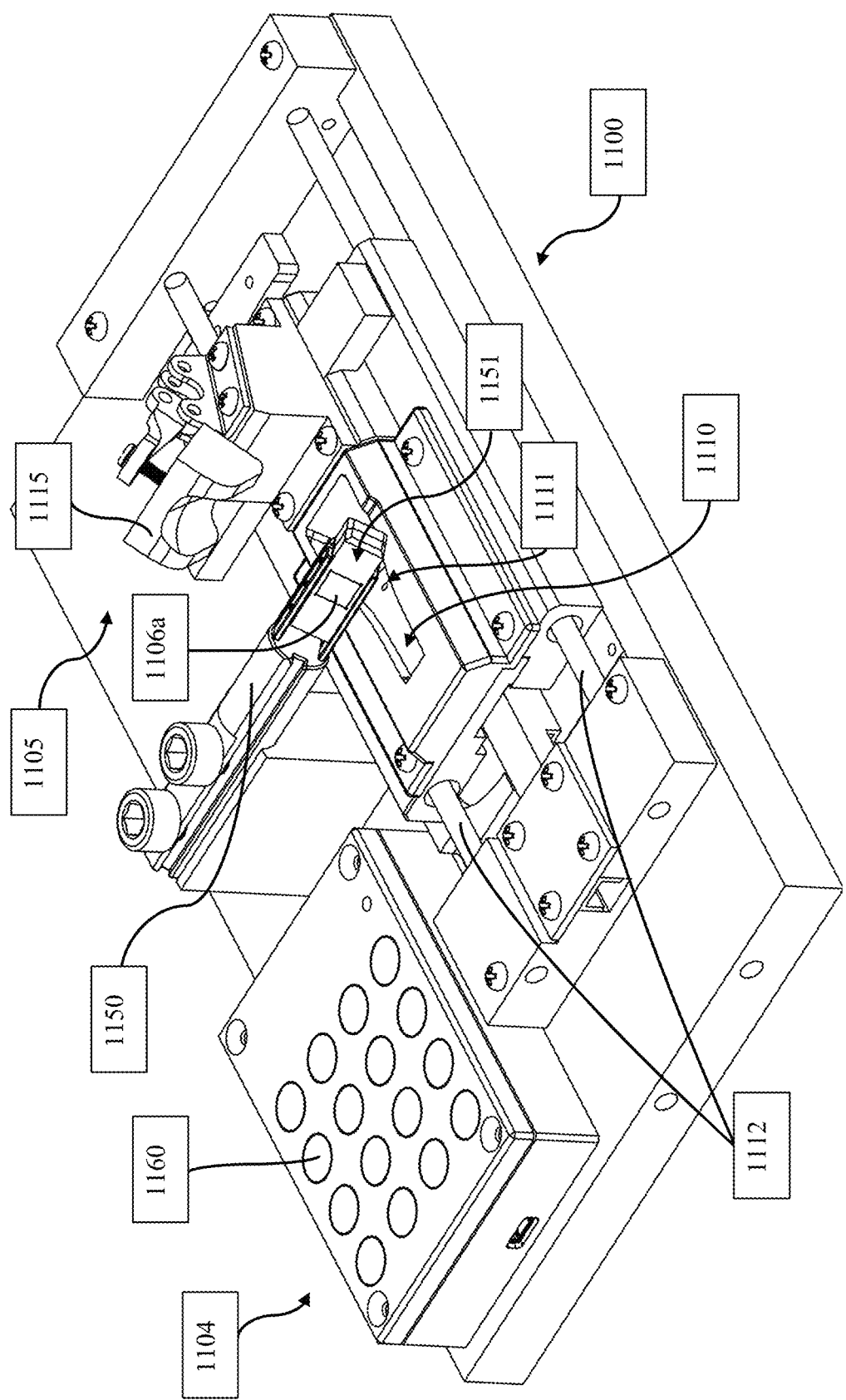
FIG. 11 shows a perspective view of a tester in accordance with another embodiment of the present invention.
Figure 12:
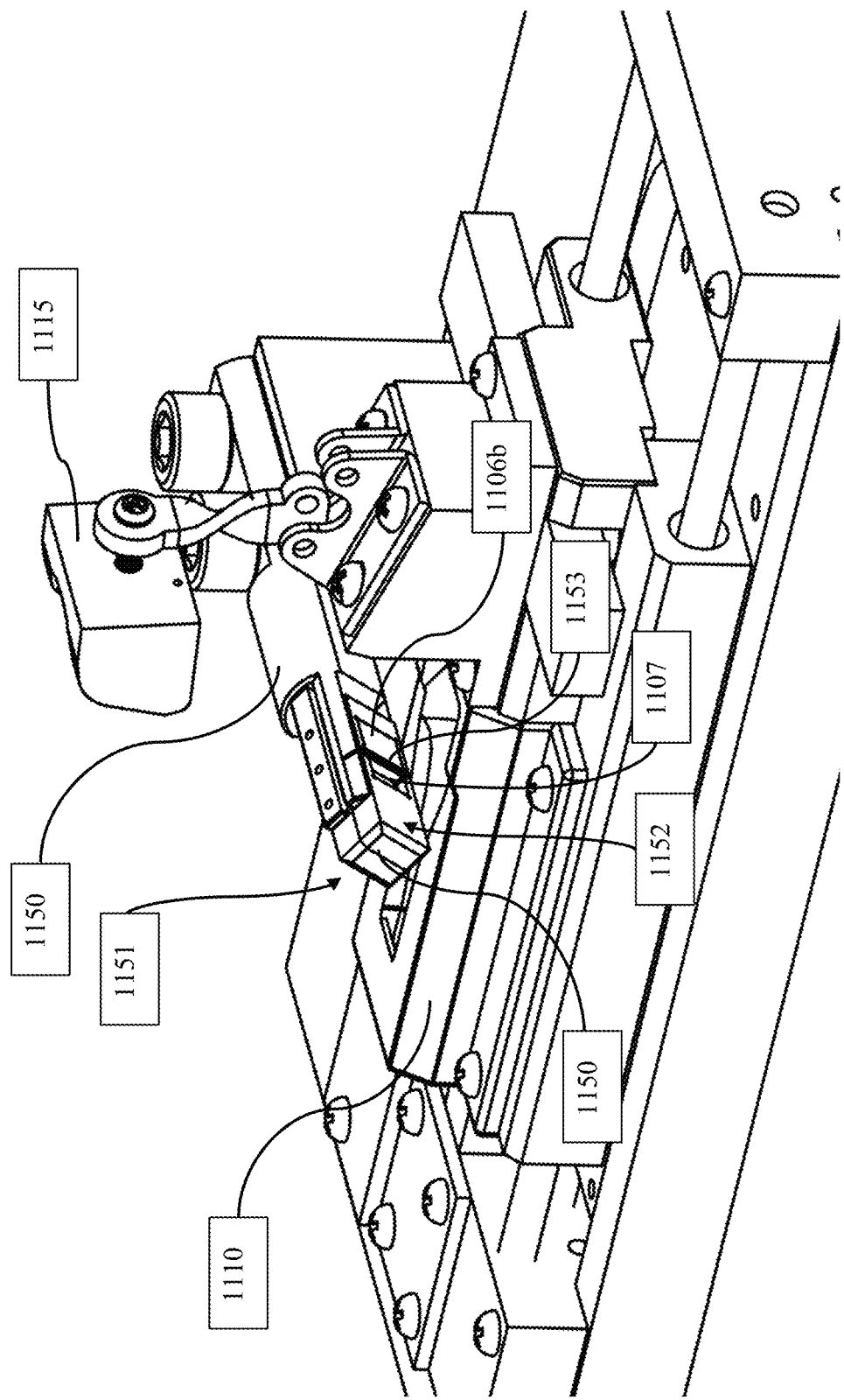
FIG. 12 shows another view of the tester device as shown in FIG. 11.

In this arrangement, the tester device 1100 comprises a tester body 1105, which can be seen in FIGS. 11 and 12 to includes a tester rod 1150 with a first side 1151 comprising a first tester detector set 1106a, and a second side 1152 comprising a second tester detector set 1106b and a tester emitter set 1107.

The tester detector sets 1106a and 1106b may comprise a set of optical filters to help identify a set of predetermined wavelengths, such as a red and an infra-red wavelength. For instance, the first tester detector set 1106a may comprise a red filter for predominantly allowing lights of 600 nm-750 nm wavelength, and an infra-red filter predominantly allowing lights of 850 nm-1000 nm wavelength through.

The tester device 1100 may be operable in a first configuration for testing a transmissive optical measuring device, and in a second configuration for testing a reflective optical measuring device.

The first tester detector set 1106a is configured to receive a set of lights from a measuring device in a first direction, and the tester emitter set 1107 is located in line with the first direction in order to deliver a set of lights to the measuring device as though the light had travelled through the tester device.

The first side 1151 and the second side 1152 may be configured to couple with a transmissive measuring device for testing. In one form, the first side 1151 and the second side 1152 may oppose each other and each comprise a substantially planar, or flat, surface for the measuring device to clamp onto, as it would in-vivo onto a user's finger. Thus, the tester device 1100 may be compatible with a transmissive optical measuring device, whereby the tester emitter set 1107 would optically couple with a measuring detector set of a measuring device and the first tester detector set 1106a would optically couple with a measuring emitter set of the measuring device.

The second tester detector set 1106b is configured to receive a set of lights from a measuring device in a second direction substantially opposing the first direction. The second tester detector set 1106b is located adjacent to the tester emitter set 1107 and optically isolated to reduce contamination of light measured by the second tester detector set 1106b or emitted by the tester emitter set 1107.

The first side 1151 as shown in FIG. 11 may comprise a substantially planar surface, below which the first tester detector set 1106a is embedded within. The second side 1152 may comprise a substantially planar surface, below which the second tester detector set 1106b and the tester emitter set 1107 are embedded within. It is noted that the surfaces need not be planar, as their configurations may depend on the geometry of the measuring device and/or the reference device.

The tester rod 1150 may further comprise an optical isolator 1153 located between the second tester detector set 1106b and the tester emitter set 1107 to reduce light leakage between the two sets of optical components. In one form, the optical isolator 1153 may protrude from the second side 1152 form an optical barrier during testing. The optical isolator 1153 may contact a surface of the measuring device during testing to substantially form an optical boundary to block or significantly reduce light transmission therebetween. The optical isolator 1153 may be compliant to assist in forming an optical seal between itself and the measuring device upon achieving contact. The optical isolator 1153 may assume a rectangular cross section of constant width extending between the second tester detector set 1106b and the tester emitter set 1107 as shown. However, it may comprise any number of other cross sections, such as a triangular or trapezoidal cross section that becomes narrower as it rises away from the second side 1152.

The optical isolator 1153 may be separately formed from the second side 1152 or the tester rod 1150 and coupled thereto, for example with an adhesive, fastener or a clip, or it may be integrally formed with the second side 1152 or the tester rod 1150.

For example, the optical isolator 1153 may comprise a foam material, or an elastomer, such as silicone or thermoplastic elastomer (TPE). The optical isolator 1153 may comprise a rectangular cross section of approximately 2 mm width and 1 mm in height above the second side, extending at least the entire length of the tester emitter set 1107 and the second tester detector set 1106b. The optical isolator 1153 may extend further to extend across and past the entire depth of the tester rod as shown in FIG. 12.

The tester device 1100 may comprise a device mount 1110 for locating a measuring device for testing. The device mount 1110 may be movable between a plurality of positions, such as from a first position to locate and/or secure a measuring device for testing, and a second position to allow the measuring device to be removed from the device mount 1110. FIGS. 13 and 14 show one such example arrangement. FIG. 13 shows the device mount 1110 in the second position wherein the measuring device 1180 is removable from the device mount 1110. FIG. 14 shows the device mount 1110 in the first position where the measuring device 1180 is located adjacent the tester rod 1150 to optically couple the tester emitter set 1107 and a tester detector set 1106b and the measuring detector set 1102 and detector emitter set 1103 respectively.

The device mount 1110 may be biased to urge the measuring device to maintain optical alignment with the tester emitter set 107 and a tester detector set 1106b and/or to form an optical seal with the optical isolator 1153. The tester device 1100 may for example comprise a spring coupled to the device mount 1110 to urge it towards the first position. In the schematic shown in FIG. 14, the spring (not shown) may urge the device mount 1110 towards A.

The device mount 1110 may be slidably movable along a base 1109 of the tester device 1100, such as along a guide 1112. In one form, the guide 1112 may comprise, or be coupled with a spring to urge the device mount 1110 in a direction, for example to urge the device towards coupling. The device mount 1110 may be movable in a direction AB as shown in FIGS. 13-14. The direction AB may be at an angle, such as between 20 and 60 degrees, such as 40 degrees, to the direction of light X from the tester emitter set 1107. Accordingly, the tester device 1100 may simulate an in-vivo configuration between the measuring device and a finger of the user, wherein the measuring device may comprise a measuring emitter set at an angle to engage with a portion of the finger on its palmer surface.

The device mount 1110 may comprise a connector 1111 for electrical communication with the measuring device. In one form, the connector 1111 may comprise a plurality of pins as shown in FIG. 11 to establish signal and/or power connections with the measuring device. The connector 1111 may be located on a base of the device mount 1110, wherein the base of the device mount 1110 comprises a cavity to receive a portion of the measuring device for easy insertion and use.

In some forms, the tester device 1100 may be configured to electrically couple with the measuring device 1180 through the connector 1111 to provide power to and/or receive a signal from the measuring device 1180, such as to determine whether the measuring device 1180 has passed a test.

The tester device 1100 may further comprise a device clamp 1115 for securing a measuring device to the device mount 1110. The device clamp 1115 may be coupled to the device mount 1110 and movable to secure the measuring device, for instance by exerting a downward pressure onto the base 1109 of the measuring device mount 1110.

In some forms of the present invention, the device mount 1110 may be removably coupled to the tester device 1100 to allow convenient conversion between a first configuration and a second configuration. The device mount 1110 may be coupled to a base 1105 of the tester device 1100 by a set of fasteners, such that in a first configuration the device mount 1110 may be removed from the tester device, and in a second configuration the device mount 1110 may be installed onto the tester device. Alternatively, or additionally, the tester device 1100 may comprise a plurality of device mounts, wherein each device mount is configured to receive a measuring device of a different shape. For example, each device mount 1110 may comprise a cavity of different shape suitable to receive a different measuring device.

In some forms, the tester device 1100 may be converted between a first configuration and a second configuration by moving the device mount 1110. In the first configuration, the device mount may be located to receive a measuring device and/or to urge the measuring device to maintain engagement with the testing rod 1150. The device mount 1110 may be movable in the first configuration between a first position to receive a measuring device and the second position to align the measuring device optically with the tester emitter set 1107 and a tester detector set 1106b. In the second configuration (not shown), the device mount 1110 may be moved to a third position, away from the tester emitter set 1107 and a tester detector set 1106a to reduce interference between the device mount 1110 and the measuring device.

In alternative arrangements, the device mount may be fixed and other components such as the testing rod may be moved and/or adjusted to achieve optical alignment for testing.

These configurations may advantageously allow convenient, reproducible and accurate testing of measuring devices with a tester device that was validated to be eligible using a different reference device.

As described elsewhere in the present document, the tester device 1100 may comprise a processor 1104 in signal communication with the tester detector sets 1106a and 1106b and the tester emitter set 1107. The processor 1104 may be configured to receive and analyse signal from the tester detector sets 1106a and 1106b and trigger the tester emitter set 1107 based on the signal, such as at a second set of wavelengths, which may include corresponding wavelengths identified by a tester detector set. The second set of wavelengths may not be identical to the set of wavelengths detected by the tester detector set.

In one form, the tester device 1100 may comprise a panel 1160 comprising a set of controls to modify one or more parameters of the tester device 1100. The set of controls may be a plurality of buttons wherein each button may be configured to change an equivalent SpO2 value of the set of lights delivered by the tester emitter set 1107.

The above description includes mere examples of one or more embodiments. It will be recognized that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A tester device for testing a measuring device, the tester comprising:
   a first light detector set and a second light detector set, wherein each light detector set is configured to detect light received thereonto and generate a signal indicative of the detected light;
   a light emitter set for outputting light; and
   a processor configured to receive and analyse the signal to identify presence of a first set of predetermined wavelengths in the detected light,
   wherein the processor is further configured to trigger the light emitter set to begin outputting light at a second set of predetermined wavelengths if at least one of the first and second light detector set is determined to have received light containing the first set of predetermined wavelengths.

2. The tester device of claim 1, wherein the first light detector set is located on a first side of the tester device and the second light detector set is located on a second side of the tester device, and the first and second sides are substantially oppose each other.

3. The tester device of claim 2, further comprising a tester rod including the first side and the second side.

4. The tester device of claim 3, the tester rod comprising an optical isolator comprising a protrusion configured to reduce light leakage between the light emitter set and the second light detector set.

5. The tester device of claim 4, wherein the optical isolator is compliant to assist in forming an optical seal between itself and the measuring device upon contact.

6. The tester device of claim 5, wherein the optical isolator is constructed from at least one of: a foam material, silicone or thermoplastic elastomer.

7. The tester device of claim 1, further comprising a device mount configured to receive the measuring device and movable between a first position to locate the measuring device for testing, and a second position to allow the measuring device to be removed from the device mount.

8. The tester device of claim 7, wherein the device mount is biased to urge the measuring device towards the first position.

9. The tester device of claim 7, wherein the device mount is slidable along a base of the test device.

10. The tester device of claim 9, wherein the device mount is movable along a direction at an angle between 20 and 60 degrees to a direction of light from the light emitter set.

11. The tester device of claim 7, the device mount comprising a cavity configured to receive a portion of the measuring device.

12. The tester device of claim 7, wherein the device mount is movable to a third position to receive a second measuring device.

13. The tester device of claim 1, further comprising a connector for electrical communication with the measuring device.

14. The tester device of claim 13, wherein the tester device is configured to provide power to and/or receive a signal from the measuring device through the connector.

15. The tester device of claim 14, wherein the tester device is configured to receive the signal from the measuring device to determine an outcome of a test for the measuring device.

16. The tester device of claim 1, wherein the first set of predetermined wavelengths comprise a first wavelength between 600 nm-750 nm and a second wavelength between 850 nm-1000 nm.

17. A tester device for testing an optical measuring device, the tester device comprising:
   a light emitter set for emitting a set of lights to the optical measuring device; and
   a plurality of light detector sets, each set of light detectors configured to receive a set of lights from the optical measuring device,
   wherein the tester device is operable in a plurality of modes to test optical measuring devices and in each of the plurality of modes the tester device is configured to test an optical measuring device with the light emitter set and one of the plurality of light detector sets to test the optical measuring device.

18. The tester device of claim 17, configured to test a transmissive pulse oximeter in a first mode and configured to test a reflective pulse oximeter in a second mode.

* * * * *